United States Patent [19]

Mercer

[11] 4,046,634

[45] Sept. 6, 1977

[54] ASSAY OF ISOENZYMES BY ION EXCHANGE CHROMATOGRAPHY

[76] Inventor: Donald W. Mercer, 451 Royce Ave., Pittsburgh, Pa. 15216

[21] Appl. No.: 677,553

[22] Filed: Apr. 16, 1976

Related U.S. Application Data

[63] Continuation-in-part of Ser. No. 473,438, May 28, 1974, abandoned, which is a continuation-in-part of Ser. No. 426,002, Dec. 19, 1973, abandoned.

[51] Int. Cl.$^2$ .................. G01N 31/04; G01N 31/08; G01N 31/14
[52] U.S. Cl. ..................... 195/103.5 R; 23/230 B; 195/66 R; 424/2
[58] Field of Search ........... 195/103.5 R, 66 R, 66 B; 23/230 B; 260/112 R

[56] References Cited
U.S. PATENT DOCUMENTS 3,234,199   2/1966   Reid ............................ 260/112 R

OTHER PUBLICATIONS

Takahashi et al., Creative Phosphokinase Isozymes of Human Heart Muscle and Skeletal Muscle. Clinica Chimica Acta. vol. 38, 1972 (pp. 285–290).
Schmidt et al., An Improved Simple Chromatographic Method for Separating the Isoenzymes of Malic Dehydrigenase and Glutomic Oxaloacetic Transaminase. Clinica Chimica Acta. vol. 15, 1967, (pp. 337–342).
Richterich et al., A Study of Lactic Dehydrogenase Isoenzyme Pattern of Human Tissues by Adsorption-Elution on Sephadex-DEAE, Clinica Chimica Acta. vol. 8, 1963, (pp. 178–192).

*Primary Examiner*—David M. Naff
*Attorney, Agent, or Firm*—Brown, Murray, Flick & Peckham

[57] ABSTRACT

A simple, rapid anion-exchange column chromatographic technique is used to determine the presence of fractions of proteins and enzymes in human serum by separating the fractions on the basis of their net electrical charges. Samples of serum of unaltered ionic strength, layered on mini columns of an ion exchange agent previously equilibrated to a low ionic strength similar to blood serum with a buffer solution, are eluted stepwise with an appropriate buffer solution having different ionic strengths at each step. Elution of the samples is without previous dialysis or other ionization treatment. Column effluents are assayed for protein content or enzyme activity by conventional means, e.g., spectrophotometric analysis. Evaluation of sera from patients utilizing these methods reveals protein fractions or isoenzyme patterns which identify specific diseases associated with the protein or isoenzyme pattern.

11 Claims, 12 Drawing Figures

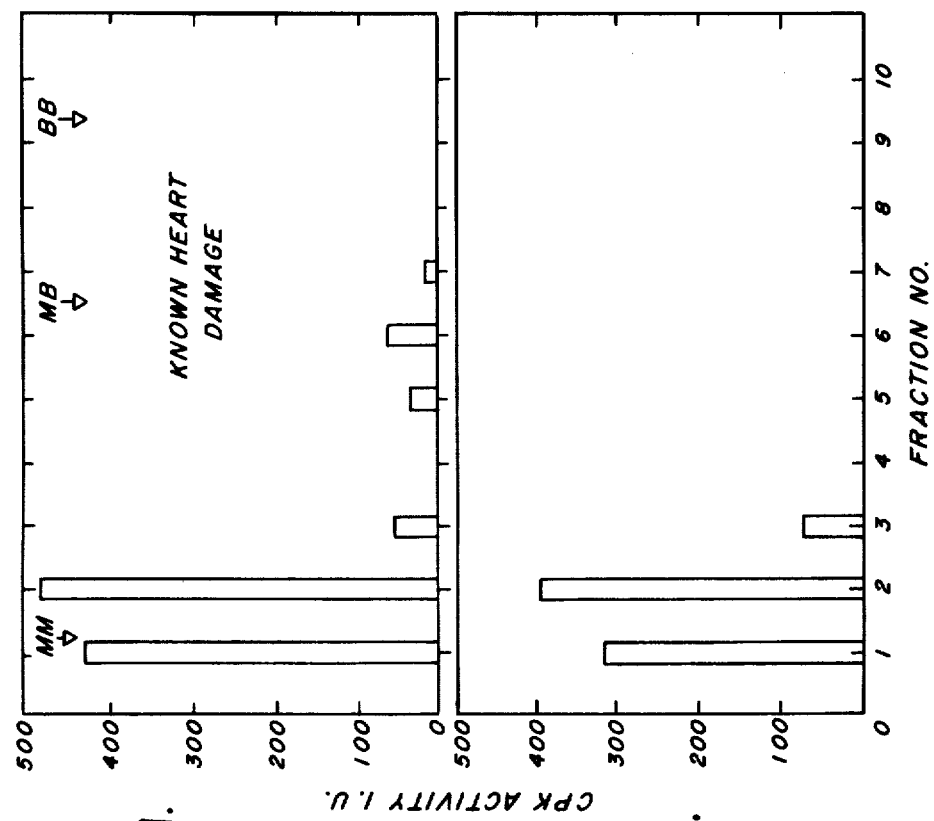
FIG. 4A.
FIG. 4B.
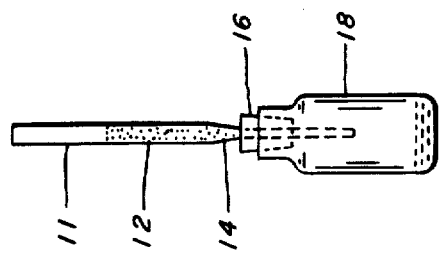
FIG. 1.

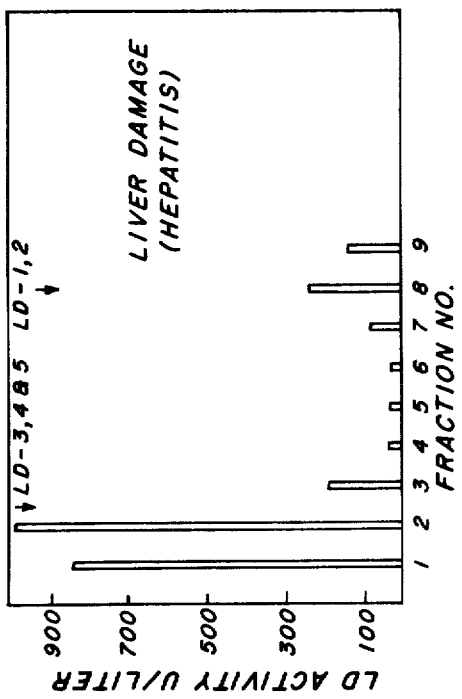
FIG. 5B. LIVER DAMAGE (HEPATITIS)
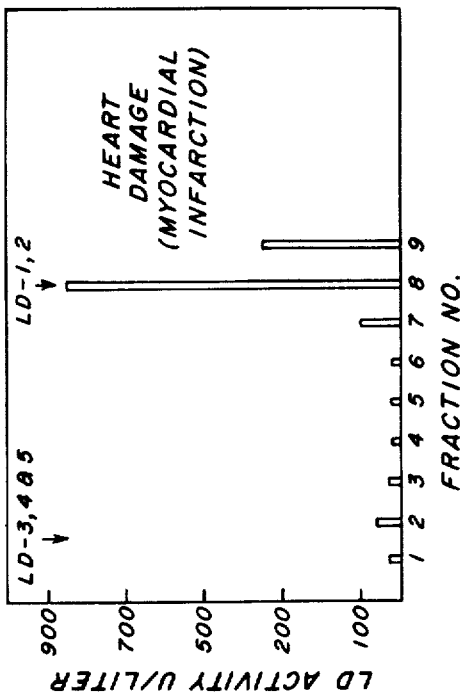
FIG. 5D. HEART DAMAGE (MYOCARDIAL INFARCTION)
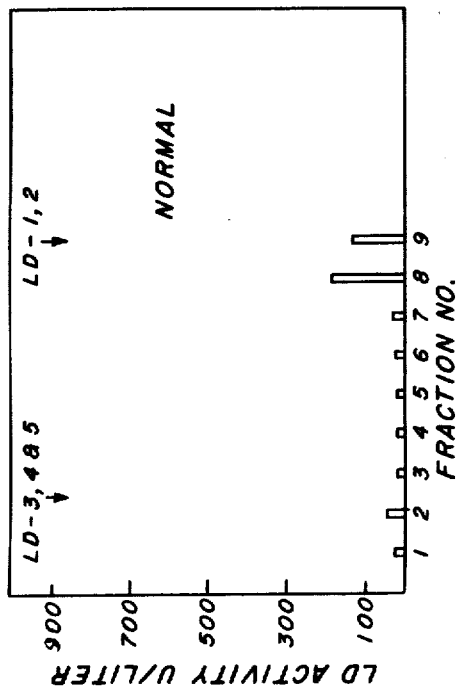
FIG. 5A. NORMAL
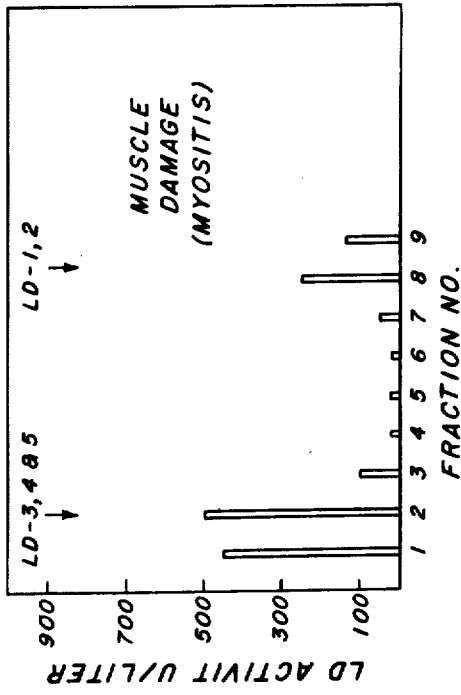
FIG. 5C. MUSCLE DAMAGE (MYOSITIS)

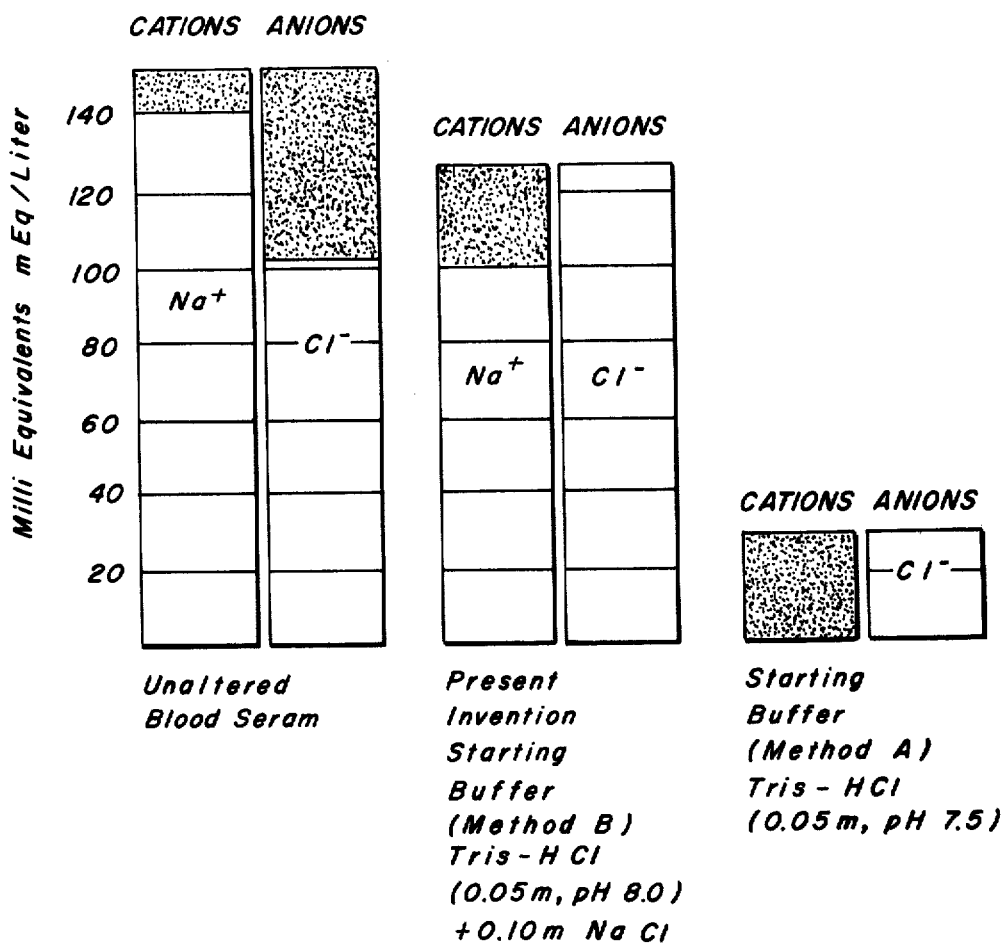

ASSAY OF ISOENZYMES BY ION EXCHANGE CHROMATOGRAPHY

CROSS-REFERENCE TO RELATED APPLICATIONS

This application is a continuation-in-part of copending application Ser. No. 473,438, filed May 28, 1974, which latter application is a continuation-in-part of application Ser. No. 426,002, filed Dec. 19, 1973 and both now abandoned.

BACKGROUND OF THE INVENTION

As is known, various diseases or injuries to the body give rise to the generation of protein fractions, e.g., isoenzymes, in blood which, if detected, can identify the particular injury or disease. For example, after a myocardial infarction, the enzyme creatine phosphokinase (CPK) is released into the blood where its activity can be measured by its ability to catalyze a specific chemical reaction. CPK has been considered to be the most reliable enzyme indicator of a myocardial infarction. The CPK activity rises in plasma about 2 to 4 hours after the infarction and persists for a period no greater than about 3 days. The enzyme lactate dehydrogenase (LDH) is also an indication of a myocardial infarction; however, this does not increase above normal until about 1 or 2 days after the infarction and reaches a maximum at about the third or fourth day, whereupon it gradually decreases until it recedes back to normal in about 10 days.

Simply determining the total rise of all fractions of CPK or LDH enzymes in the blood serum is not an accurate method of diagnosis. For example, total CPK elevations can occur due to noncardiac conditions such as chronic alcoholism, cardioversion, cerebrovascular diseases, hypothyroidism, intramuscular injections and surgical trauma. A total rise in LDH can occur from either liver damage (e.g., hepatitis), a myocardial infarction, or muscle damage (e.g., myositis).

Both the CPK and LDH enzymes, as well as other enzymes, contain various fractions or isoenzymes of different net electrical charge. A rise in specific ones of these isoenzymes will, in contrast to a total rise in LDH or CPK, indicate a myocardial infarction or other diseased organ. The CPK enzyme contains the fractions or isoenzyme types MM, MB and BB. A rise in the MM and MB isoenzymes indicates a myocardial infarction; a rise in the MM isoenzyme indicates muscle damage only; whereas a rise in the BB-type only indicates brain damage. Similarly, LDH is composed of five isoenzymes (LD-1, LD-2, LD-3, LD-4 and LD-5), all of which appear in varying amounts dependent upon the type of tissue damage. Patient sera containing elevated amounts of LD-1 and LD-2 indicate a myocardial infarct; while elevated fractions of LD-3, LD-4 and LD-5 indicate damaged liver or muscle tissue.

The chief aim of past work has been to separate isoenzymes of CPK and LDH, as well as isoenzymes of other enzymes present in blood serum, by conventional electrophoretic techniques. However, routine use of the electrophoretic technique is limited since laborious gel preparations and poor staining techniques remain an integral part of the electrophoretic procedure.

Attempts have also been made to separate various isoenzymes with the use of ion exchange chromatography. Such attempts are described, for example, in an article by Ellen Schmidt, appearing in *Clinica Chimica Acta*, 15 (1967), pages 337-342. Sodium phosphate is used as a buffer in the ion exchange chromatographic technique described in the aforesaid article; and this requires dialysis of the fresh sera for at least six hours against a 0.008 molar potassium phosphate solution. Furthermore, the chromatographic technique described in that article takes at least 2 to 4 hours. As a result, while the method described in that article may be satisfactory for experimental studies, it is not satisfactory for rapid, routine use in a clinical laboratory by relatively unskilled technicians.

Takahashi et al., Clin. Chimica, Acta 38, 285-290 (1972) disclose a five-step process utilizing ion exchange chromatography to separate isoenzymes. The Takahashi et al. process requires about 8 to 9 hours to complete since it depends upon dialysis of the sample to equilibrate it to the column used. Takahashi et al. use a DEAE-Sephadex column and elute the sample by gradient elution. The Takahashi et al. process is time consuming and causes difficulty in obtaining satisfactory results.

Richterich et al., Clinica Chimica Acta, 8, 178-192 (1963) disclose a batch elution technique wherein undialyzed serum is mixed with DEAE-Sephadex in a test tube and centrifuged. This process is time consuming and difficult to carry out since it requires repeated centrifugation steps and is not satisfactory for rapid, routine use in a clinical laboratory.

SUMMARY OF THE INVENTION

In accordance with the present invention, a new and improved method is provided for isolating specific protein fractions and specific isoenzymes, in human serum, which method does not require prior dialysis of the serum and is rapid and accurate such that it can be performed by relatively unskilled laboratory personnel. More particularly, this invention is applicable to the separation into isoenzymes of the followng typical enzyme systems; creatine phosphokinase (CPK), lactate dehydrogenase (LDH), acid phosphates, aspartate transaminase, gamma glutamyl transpeptitase, amylase, aldolase and the like. Other blood proteins which can be fractioned are, for example, lipoproteins and gamma globulins.

Specifically, in carrying out the invention, the presence of proteins or isoenzymes of different net electrical charge is determined in blood serum or in body tissues by the following sequential steps: (a) passing a sample of the serum or tissue extract, in unaltered ionic form, through an ion exchange agent which had previously been equilibrated so that its net electrical characteristics are essentially the same as either the blood serum or the tissue extract and collecting the effluent. This is important since it prepares the ion exchanger for the addition of serum. This preparation or equilibration of the ion exchanger provides the conditions for optimal separation of serum, proteins and isoenzymes. It is not necessary that the equilibration result in a column which has the exact electrical characteristics of the sample, however, a close approximation is preferred. (b) passing through the thus-treated ion exchange agent successive volumes of a buffer solution and collecting separately the effluent from each volume, the molar ion concentration of certain of the separate volumes of buffer solution is different than that of the others to cause proteins or isoenzymes of different net electrical charge to be present in the separate effluents and (c) analyzing each of the separate volumes of effluent to determine whether the blood serum or tissue extract contains proteins or isoenzymes of predetermined net electrical charge. Various assay methods are available but preferred is spectrophotometric analysis wherein the absorbence of light energy for a given wavelength is measured for a solution containing at least a portion of each volume, whereby the relative absorbence of the respective volumes is an indication of the presence of isoenzymes or protein fraction.

The invention is applicable to many protein enzyme systems in human blood serum or tissue extracts but for illustration the process of determining CPK and LDH isoenzymes in blood serum will be described.

As will be seen from the following detailed description, the buffer solution is preferably a solution of a buffer at pH 8.0 to 9.5 having characteristics which allow it to be diluted mixed with various concentrations of a salt to enable it to impart to an ion exchange column, upon equilibration, net electrical charge characteristics essentially the same as blood serum. Tris-(hydroxymethyl) aminomethane hydrochloride (Tris-HCl) and sodium chloride (i.e., a Tris-buffered NaCl solution) is the preferred buffer since it has essentially the same electrical charge characteristics as blood serum when the Tris-HCl is 0.05 M and the NaCl is 0.1 M. The electrical charge characteristics of blood serum are noted in Pitts, Physiology of the Kidney and Body Fluids, Yearbook Medical Publications, Chicago, 1963. After initially passing the blood serum through the ion exchange agent, equal volumes of Tris-buffered sodium chloride solution of about 0.1 molar concentration of sodium chloride are passed through the ion exchange agent a number of times and the effluent from each volume collected. Thereafter, a plurality of volumes of a Tris-buffered sodium chloride solution of about 0.2 molar concentration of sodium chloride are passed through the ion exchange agent and again the effluents are collected. The chromatographic technique takes only 15 minutes to perform. Thereafter, the separate effluents are assayed. In cases wherein CPK and LDH are being assayed, the Rosalki CK method is used to determine the presence of specific isoenzymes (e.g., MM and MB types) and the Wacker LDH method is used to determine the presence of LD-1 through LD-5 isoenzymes.

The ion exchangers are preferably anion exchangers of the amine type based on a polysaccharide matrix. Typical of such materials are DEAE-Sephadex and QAE-Sephadex. The Sephadex ion exchangers are synthetic, organic compounds, derived from the polysacchride, dextran. DEAE-Sephadex is the diethylaminoethyl derivative of Sephadex and is a weakly basic anoin exchanger. QAE-Sephadex is the diethyl-(2-hydroxypropyl)-amino ethyl derivative of Sephadex and is a weakly basic anion exchanger. The Sephadex ion exchanger are available from Pharmacia Fine Chemicals, Piscataway, New Jersey. Similar ion exchangers with ionic properties and flow-through characteristics are suitable for use in this invention.

The use of only two different molar ion concentrations of the Tris-buffered sodium chloride (other alkali metal salts such as potassium chloride are equally suitable) solution will act to separate, in various effluents, all of the CPK and LDH isoenzymes present in blood serum. These include all the LDH isoenzymes and the MM and MB isoenzymes of CPK. The BB isoenzyme requires the use of a third buffer agent of 0.3 molar concentration sodium chloride, in which case three different buffer solutions (of 0.1 to 0.2 and 0.3 molar concentration of sodium chloride, respectively) must be passed through the ion exchange agent containing a sample of brain tissue extract or blood serum from the patient. Instead of Tris-HCl, Tris-glycine can be used if a pH higher than 8 or 9 is needed.

It has been found that for CPK and LDH, the buffer used for equlibration must have a pH of 8.0 when the Tris-HCl is 0.05 M and the NaCl is 0.1 M. The same buffer at pH 8 is also required for equilibrating the column for acid phosphatase, gamma glutamyl transpeptitase and gamma globulin assays when the ion exchange column used is DEAE-Sephadex. A buffer of pH 9 having 0.5 M Tris-HCl and 0.1 M NaCl is needed for equilibrating the column for aspartate transaminase, amylase, and aldolase assays when the column used is QAE-Sephadex.

The above and other objects and features of the invention will become apparent from the following detailed description taken in connection with the accompanying drawings which form a part of this specification, and in which:

FIG. 1 is an illustration of one type of column (Pasteur pipette) utilized in the present invention and containing an ion exchange agent being collected in a vial;

Figure 3:
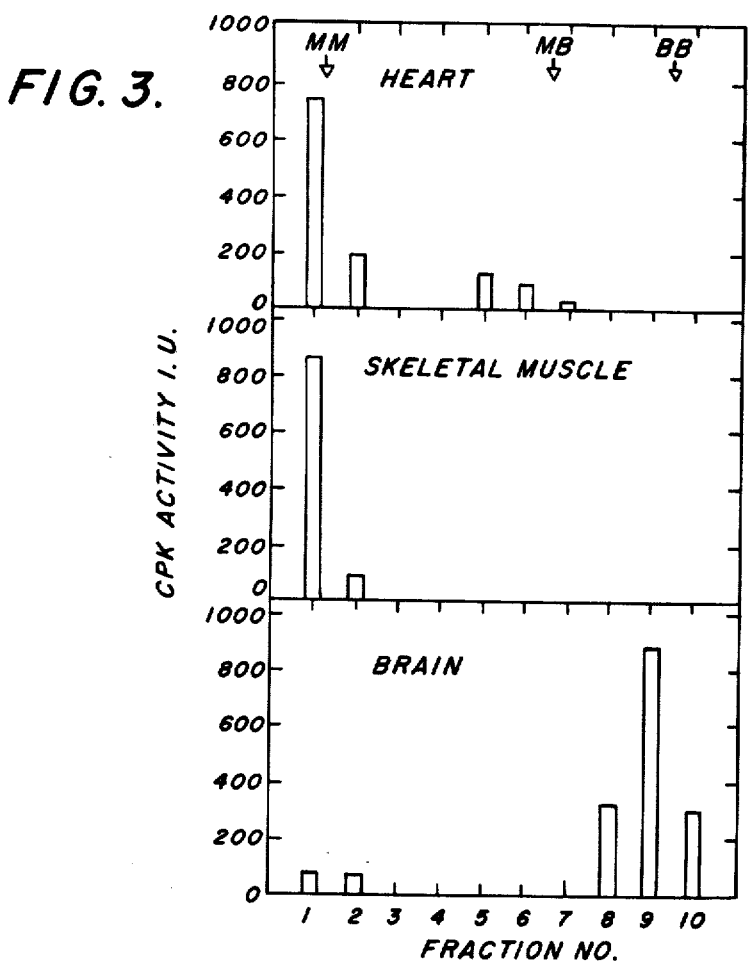
Figure 6:
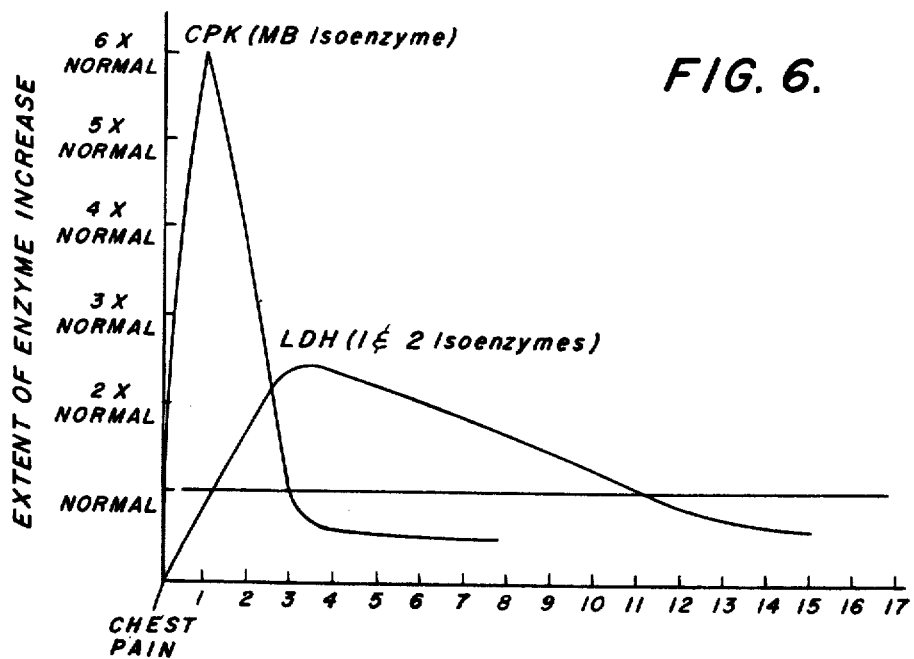

FIG. 3 comprises graphs showing the CPK column chromatographic results obtained on heart, skeletal muscle and brain tissue extracts subjected to the ion exchange process of the invention;

FIG. 4A is a graph illustrating the CPK column chromatographic results obtained after subjecting blood serum, obtained from patients having known myocardial infarctions, to the process of the invention;

FIG. 4B is a graph illustrating the CPK column chromatographic response of sera, obtained from patients who did not have a myocardial infarction, which were subjected to the process of the invention;

FIG. 5A is a graph illustrating the LDH column chromatographic results obtained after subjecting blood serum, obtained from a normal patient, to the process of the invention;

FIG. 5B is a graph, similar to that of FIG. 5A, illustrating the LDH fractions obtained from the blood serum of a patient having hepatitis;

FIG. 5C is a graph illustrating the LDH column chromatographic results obtained from the blood serum of a patient suffering from muscle damage (myositis);

FIG. 5D is a graph illustrating the LDH column chromatographic results obtained from the blood serum of a patient with heart damage (myocardial infarction);

FIG. 6 is a graph illustrating typical changes in serum CPK-type MB and LDH-type LD-1, 2 isoenzymes following a myocardial infarction; and FIG. 7 is a graph showing the comparative ionic compositions of blood serum and various starting buffers.

In carrying out the invention, a sample of blood is taken from a patient and permitted to clot. Thereafter, it is subjected to a conventional centrifuge process wherein the blood serum or plasma is separated from the blood cells. Preferably the sample is blood serum. Alternatively, in the case of a tissue sample, it is first homogenized and then centrifuged to obtain the tissue extract. Thereafter, a sample of the serum, plasma or tissue extract is passed through an ion exchange column such as that shown in FIG. 1. It typically comprises a 5-inch Pasteur pipette half filled with an ion exchanger 12, however, larger or smaller columns are suitable as long as the dimensions are such that maximum flow rates are achieved. Beneath the ion exchanger 12 is a glass wool plug 14, the pipette passing through a rubber stopper 15 fitted in the mouth of a collection vial 18.

The ion exchange agent 12 is of the anion type, preferably being of the amine type based on a polysaccharide matrix. The type of anion ion exchange agent which can be used can be varied to suit requirements; however, DEAE-Sephadex (Trademark) and QAE-Sephadex manufactured and sold by Pharmacia Laboratories, Inc. of Piscataway, New Jersey have been found to be suitable with DEAE-Sephadex preferred.

Figure 2A:
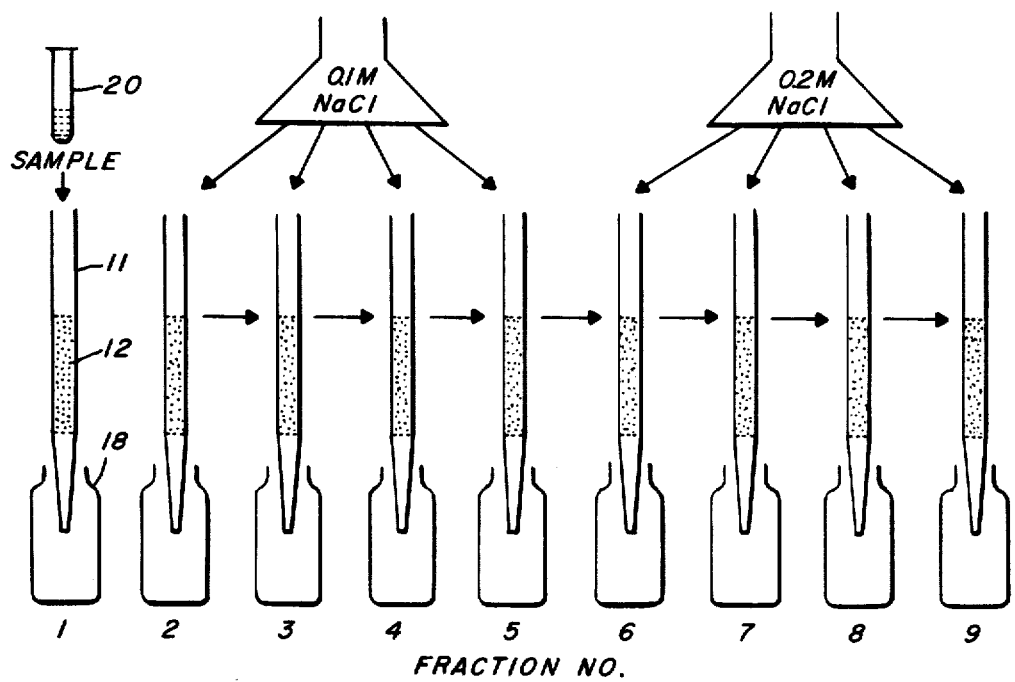
FIG. 2A is a flow diagram illustrating the process of the invention as applied to the simultaneous separation of both CPK and LDH isoenzymes from blood plasma using buffers of two different molar ion concentrations.

A flow diagram of the process of the invention for simultaneously separating CPK and LDH isoenzymes from blood plasma is shown in FIG. 2A wherein nine separate vials Nos. 1–9 are shown. It should be understood, however, that while nine separate pipettes are shown in FIG. 2A, only a single pipette is inserted in succession into each of the vials 1–9 such that the effluent passing therethrough, while it is inserted into a particular vial, will be collected within that vial.

As shown in FIG. 2A, the process starts by initially causing the sample, identified by the reference numeral 20, to pass through the pipette 11 and the ion exchange agent 12 therein. Prior to passing the sample 20 through the ion exchange agent, the ion exchange agent is equilibrated preferably with 50 mmol/liter Tris-HCl, pH 8.0* containing 100 millimolar sodium chloride. As the blood serum passes through the ion exchange agent 12 while the pipette is fitted within the first vial 1, the MM-CPK isoenzymes of serum will pass therethrough while the remaining CPK isoenzymes MB-BB types will adhere to the exchange agent due to their net electrical charge. Thereafter, the pipette 11 is transferred to the second vial 2 where a 1-milliliter fraction or volume of Tris-buffered (0.050 molar, pH 8.0) sodium chloride (0.1 molar) is caused to pass through the ion exchange agent 12 with the effluent being collected in vial 2. This process is repeated with the pipette 11 being transferred in succession to vials 3, 4, and 5. Thereafter, the effluent from four 1-milliliter fractions of Tris-buffered (0.050 molar, pH 8.0) sodium chloride (0.2 molar) are collected in vials 6, 7, 8 and 9. A flow rate of about ½ milliliter per minute is maintained throughout the elution. The total elution time is approximately 15–20 minutes.
*pH 9.0 in the case of aspartate transaminase, amylase or aldolase with QAE-Sephadex.

The process shown in FIG. 2A, while suitable for the separation of MM and MB type CPK isoenzymes from blood serum, cannot be used to detect the BB-type isoenzyme present in brain tissue. When the separation and detection of BB-type isoenzyme is desired, the process of FIG. 2B must be used. The process of FIG. 2B can also be used with blood plasma; however it is not preferred because of the requirement for a third, different molar ion concentration of the buffer solution.

With reference to FIG. 2B, serum 20 is again caused to pass through the ion exchange agent in pipette 11 previously equilibrated with the Tris-buffered sodium chloride solution of 0.1 molar concentration. The remainder of the purpose is the same except that 1-milliliter fractions of a buffer solution of 0.1 molar concentration are caused to pass through the pipette 11, the effluents being collected in vials 2–4. It should be understood, however, that in the case of blood serum containing very high CPK concentrations, it may be necessary to pass additional volumes of the 0.1 molar concentration buffer through the pipette. Thereafter, the same volumes of a buffer solution of 0.2 molar concentration are caused to pass through the pipette three times and the effluents collected in vials 5–7. Finally, three 1-milliliter fractions of 0.3 molar concentration are caused to pass through the pipette three times and the effluents collected in vials 8–10. The 0.3 molar concentration buffer is required in this case because of the ionic charge of the type BB-CPK isoenzyme which is higher than the other CPK isoenzymes and all of the LDH isoenzymes.

In either case (i.e., FIG. 2A or 2B), all column effluents including that in the first vial are assayed by both the Oliver-Rosalki CPK method and the Wacker LDH method. For thus purpose, an ESKALAB (trademark) spectrophotometer of the type manufactured by Smith, Kline Instruments, Inc. of Palo Alto, California can be used. In the spectrophotometric technique, a suitable reagent such as that specified by Smith, Kline Instruments, Inc. for LDH determination, for example, is mixed with samples of the effluent derived from each of the vials shown in FIG. 2A or 2B. The samples of the reagent-containing effluent are then heated in an incubator, and the mixture is then exposed to a beam of ultraviolet light energy at 340 nm. The increase in absorbence of the mixture per unit time (min.) is followed. This measurement is then expressed in international units (IU) which is that amount of enzyme which catalyzes the transformation of 1 micromole of reagent (enzyme substrate) per minute. The process is then repeated for CPK determination using a different reagent.

Figure 2B:
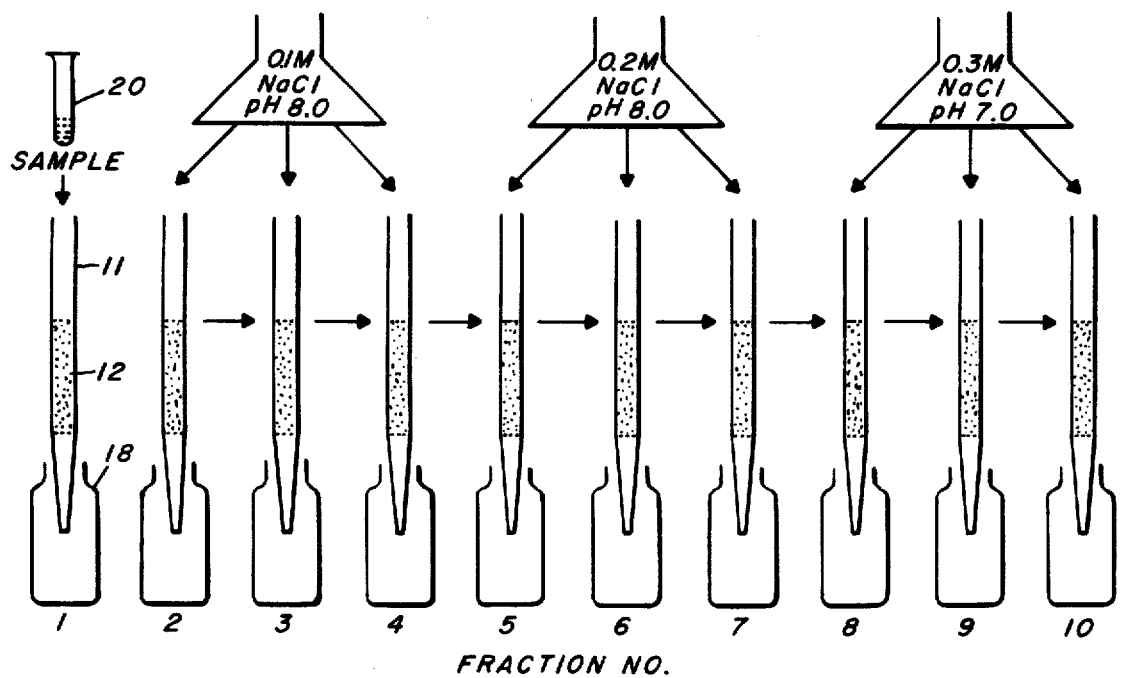
FIG. 2B is a flow diagram illustrating the process of the invention for the separation of fractions of the CPK isoenzymes present in blood serum or brain tissue using buffers of three different molar ion concentrations.

It has been found that the various vials shown in FIG. 2A or 2B will contain varying types of CPK and LDH isoenzymes, depending upon their net electrical charge. In this regard, it has been found that the type-MM CPK isoenzyme from skeletal muscle will be found in vials or fractions 1, 2 and 3 of FIGS. 2B; type-BB from the brain will be found in vials or fractions 8–10; and type-MB, due to a myocardial infarction will be found in fractions 5, 6, and 7. This is perhaps best illustrated in FIG. 3 wherein column chromatographic results, based on CPK activity in international units (IU), are shown for homogenized tissue samples from the heart, skeletal muscle derived from the heart, both the MM-type and MB-type CPK isoenzyme are derived. The MM-type appears in fractions 1 and 2; whereas the MB-type appears in fractions 5, 6, and 7. In the case of skeletal muscle, only the MM-type isoenzyme occurs in fractions 1 and 2. Finally, in the case of brain tissue, the type-MM CPK isoenzyme appears, to a very limited degree, in fractions 1 and 2. The type-BB isoenzyme, however, appears heavily in fractions 8, 9 and 10. It can be seen that the type-MB CPK isoenzyme occurs only in heart tissues as contrasted with skeletal muscle and brain tissue, notwithstanding the fact that all of these tissues contain some type of CPK isoenzyme. Without the technique of the present invention wherein the serum or plasma is subjected to varying molar concentrations of Tris-buffered sodium chloride or another similar buffer agent, it would not be possible to distinguish the type-MB CPK isoenzyme from the other types in order to determine the existence of a myocardial infarction.

FIG. 4A shows typical CPK ion exchange isoenzyme patterns of serum obtained from patients who had known myocardial infarctions. Note that fractions 1 and 2 show material amounts of type-MM CPK activity, with fractions 3 showing a lesser amount. This conforms to the CPK activity for heart tissue shown in FIG. 3. Additionally, however, in the case of blood serum taken from patients having known myocardial infarctions, considerable portions of CPK activity due to MB-type enzymes occur in fractions 5, 6 and 7, again conforming to the experimental data shown in FIG. 3.

In FIG. 4B, ion exchange isoenzyme patterns are shown of serum from patients suffering from renal failure, hypothyroidism, cerebrovascular disease, pulmonary disease, I.M. injections, chronic alcoholism, accidents and patients in postoperative recovery. Note that in this case, only the MM-type CPK isoenzyme has been detected. Although the MM isoenzyme is the predominant peak in the patterns of both FIGS. 4A and 4B, only in sera of patients with myocardial infarctions is the MB isoenzyme detected.

When the process of FIG. 2A is employed with only nine vials and two buffer solutions of differing molar concentrations, the type-MM isoenzyme of CPK appears in fractions 1, 2, 3 and 4 while the type-MB isoenzyme will appear in fractions 7, 8 and 9.

FIGS. 5A–5D show typical ion exchange LDH isoenzyme patterns of serum from patients, three of whom suffered from various maladies. FIG. 5A shows the pattern for serum from a normal patient. The levels of all isoenzymes LD-1 through LD-5 are low, with those of the LD-1 and LD-2 types being slightly higher than the others. In FIG. 5B, the serum obtained from a patient suffering from hepatitis shows an abnormally high level for the LD-3, LD-4 and LD-5 types. The serum from a patient with muscle damage (FIG. 5C) shows a pattern similar to that of FIG. 5B except that the level of types LD-3, LD-4 and LD-5 is below that of FIG. 5B and above that of a normal patient (FIG. 5A). FIG. 5D shows the pattern derived from a patient who has suffered from a myocardial infarction. Note that fractions LD-1 and LD-2 are excessively elevated while the remainder appear as they do in a normal patient.

The following Table I is a tabulation of the diagnosis of seventy-one patients to serum CPK isoenzyme distribution.

TABLE I

SERUM CPK ISOENZYMES IN PATIENTS WITH ELEVATED CPK (OVER 6 × NORMAL)

| Diagnosis | No. of Patients | CPK ISOENZYMES | | |
|---|---|---|---|---|
| | | MM | MB | BB |
| Myocardial infarction | 35 | 35 | 35 | 0 |
| Acute renal failure | 4 | 4 | 0 | 0 |
| Hypothyroidism | 1 | 1 | 0 | 0 |
| Cerebrovascular disease | 8 | 8 | 0 | 0 |
| Pulmonary disease | 2 | 2 | 0 | 0 |
| Chronic alcoholic | 2 | 2 | 0 | 0 |
| Muscular injections | 1 | 1 | 0 | 0 |
| Postoperative recovery | 1 | 1 | 0 | 0 |
| Muscle cramps | 1 | 1 | 0 | 0 |
| After cardioversion | 1 | 1 | 0 | 0 |
| Accident victims | 6 | 6 | 0 | 0 |
| Other diagnoses | 9 | 9 | 0 | 0 |

All patients in the group had blood serum containing CPK over six times normal. Note that out of the 35 patients having a known myocardial infarction, MM and MB isoenzymes were detected in each case. However, in the remaining patients having different diagnoses, only the MM-type isoenzyme was detected, but not the MB-type. Thus, by detecting the MB-type isoenzymes in accordance with the teachings of the invention, an accurate and reliable diagnosis of myocardial infarction can be made.

Results of quantitative analysis for MM and MB in 20 patients with myocardial infarction are shown in Table II.

TABLE II

QUANTITATIVE ANALYSIS OF CPK ISOENZYMES IN 20 PATIENTS WITH A DIAGNOSIS OF MYOCARDIAL INFARCTION

| Patient | MM U/liter | MB U/liter | % MB[a] |
|---|---|---|---|
| 1 | 1762 | 124 | 7 |
| 2 | 864 | 56 | 6 |
| 3 | 1246 | 50 | 4 |
| 4 | 837 | 103 | 12 |
| 5 | 654 | 42 | 6 |
| 6 | 1101 | 43 | 4 |
| 7 | 926 | 89 | 9 |
| 8 | 550 | 55 | 9 |
| 9 | 1218 | 46 | 4 |
| 10 | 1010 | 48 | 5 |
| 11 | 774 | 68 | 8 |
| 12 | 1054 | 62 | 5 |
| 13 | 1365 | 110 | 8 |
| 14 | 1247 | 42 | 3 |
| 15 | 796 | 16 | 2 |
| 16 | 1232 | 123 | 11 |
| 17 | 918 | 23 | 2 |
| 18 | 1139 | 96 | 9 |
| 19 | 857 | 78 | 9 |
| 20 | 1157 | 101 | 9 |

[a]MB/MM + MB × 100

Isoenzyme analysis was performed on specimens collected during peak activity of total CPK without regard to specified post-infarct time periods. An average yield of 6% for MB isoenzyme was consistent with activities (approximately 10%) of MB found in cardiac tissue. Correlation between MB yields and total CPK was not observed.

A typical time course for post-infarct activities of type-MB CPK and types LD-1 and LD-2 of LDH is shown in FIG. 6. Note the MB isoenzymes of CPK rises abruptly from the onset of chest pain, reaching the level of six times normal in about 24 hours. It then recedes back to normal in about three days. The LDH isoenzymes LD-1 and LD-2, rise much slower after the onset of a myocardial infarction, reaching a level of over two times normal in about 3 days and then receding back to normal in about eleven days after the infarct. By monitoring these isoenzyme levels, therefore, the existence of a myocardial infarct can be accurately diagnosed.

Column reproducibility was evaluated by repeated analysis of a serum pool fortified with MB isoenzyme from an extract of heart tissue. A sample volume of 1 ml. containing 748 mU of CPK, was applied to each of 10 ion-exchange columns. The results (Table III) proved to be satisfactory, and excellent recoveries of total CPK from the columns were also observed (Table II).

TABLE III

VARIATION OF ISOENZYME DISTRIBUTION IN SPECIAL MB FORTIFIED SERUM CONTROL WITH MULTIPLE DETERMINATIONS

| Sample No. | MM U/liter | MB U/liter | % Recovery |
|---|---|---|---|
| 1 | 592 | 77.0 | 89 |
| 2 | 700 | 73.5 | 103 |
| 3 | 594 | 74.4 | 89 |
| 4 | 672 | 79.2 | 100 |
| 5 | 661 | 77.4 | 99 |
| 6 | 635 | 77.0 | 95 |

TABLE III-continued
VARIATION OF ISOENZYME DISTRIBUTION IN SPECIAL MB FORTIFIED SERUM CONTROL WITH MULTIPLE DETERMINATIONS

| Sample No. | MM U/liter | MB U/liter | % Recovery |
|---|---|---|---|
| 7 | 599 | 70.0 | 89 |
| 8 | 631 | 76.6 | 95 |
| 9 | 680 | 71.3 | 100 |
| 10 | 609 | 67.3 | 90 |
| Mean | 638 | 74.4 | 95 |
| S.D. | 39.2 | 3.81 | — |

The criticality of the concentration and pH values of the various buffer solutions utilized in practicing the invention is shown in Table IV which is a comparison of the method of the instant invention (Method A) with that of a slightly different method (Method B). The buffers used in the respective methods were as follows:

| | Method A* | Method B** |
|---|---|---|
| 1. Equilibration and MM buffer | Tris-HCl (0.05 M, pH 7.5) | Tris-HCl (0.05 M, pH 8.0) + 0.10 M NaCl |
| 2. MB buffer | Tris-HCl (0.05 M, pH 7.5) + 0.15 M NaCl | Tris-HCl (0.05 M, pH 8.0) + 0.20 M NaCl |
| 3. BB buffer | Tris-HCl (0.05 M, pH 7.5) + 0.3 M NaCl | Tris-HCl (0.03 M, pH 7.0) + 0.30 M NaCl |

*0.25 ml. sample applied to the column.
**0.500 ml. sample applied to the column.

TABLE IV
COMPARISON OF METHODS A AND B FOR SEPARATION OF MB AND BB ISOENZYMES

| | Total CK | Method A MB | Method B MB |
|---|---|---|---|
| Patients without myocardial infarction | | | |
| Hypothyroidism | 778 | 85 | 8.0 |
| Intramuscular Injection | 616 | 26 | 2.4 |
| Alcoholism | 328 | 17 | 3.5 |
| Acute Renal Failure | 965 | 64 | 6.0 |
| Alcoholism | 225 | 20 | 2.2 |
| Postoperative Recovery | 416 | 19 | 2.6 |
| Postoperative Recovery | 921 | 44 | 6.4 |
| Patients with myocardial infarction | | | |
| | 611 | 73 | 50 |
| | 742 | 70 | 54 |
| | 1965 | 160 | 140 |
| | 1905 | 156 | 176 |
| | 613 | 35 | 11 |

| | Total CK | Method A MB | Method B MB | Method A BB | Method B BB |
|---|---|---|---|---|---|
| | | % of Total CK | | U/liter | |
| Patients without myocardial infarction | | | | | |
| Hypothyroidism | 778 | 10.9 | 1.0 | 36 | 0.5 |
| Intramuscular Injection | 616 | 4.2 | 0.3 | 10 | 1.5 |
| Alcoholism | 328 | 5.1 | 1.1 | 7 | 0.8 |
| Acute Renal Failure | 965 | 6.6 | 0.6 | 29 | 1.3 |
| Alcoholism | 225 | 8.9 | 0.9 | 10 | 0.9 |
| Postoperative Recovery | 416 | 4.6 | 0.6 | 19 | 0.7 |
| Postoperative Recovery | 921 | 4.8 | 0.6 | 14 | 0.6 |
| Patients with myocardial infarction | | | | | |
| | 611 | 11.9 | 8.1 | 52 | 2.2 |
| | 742 | 9.4 | 7.3 | 55 | 1.8 |
| | 1965 | 8.1 | 71.1 | 112 | 3.6 |
| | 1905 | 8.2 | 9.2 | 128 | 4.1 |
| | 613 | 5.7 | 3.6 | 17 | 0.6 |

From the data in the foregoing Table IV, it can be seen that there is a considerable MM isoenzyme carry-over utilizing the Method A process. This is best demonstrated with sera of patients without myocardial infarction but with elevated total serum CPK due to various non-cardiac conditions. In samples of this type, electrophoretic analysis of the Method A column MB fraction confirms the MM carry-over—an electrophoretic band of MM in the MB fraction. The magnitude of MM carry-over is demonstrated by CPK activity in the Method A MB fraction which is four to 13 times the values obtained utilizing the teachings of this application (Method B). When MB values are expressed as percent of total CPK, the MB values (0.30 to 1.1% obtained with the practice of the invention of Method B) are within normal limits (less than 2%) established for MB isoenzyme in healthy laboratory technicians and hospitalized patients with a variety of non-cardiac conditions. The foregoing Table IV shows that the Method A MB values in patients without myocardial infarction are markedly above normal levels (4 to 11%).

Utilizing Method A, the MB values obtained would not enable one to accurately distinguish between a cardiac and non-cardiac condition. The MB isoenzyme carry-over into Method A's BB fraction is best demonstrated in cardiac patients with elevated MB values. Electrophoretic analysis of the BB fraction confirms that there is an MB carry-over. Considering the significant amounts of MM and MB carry-over in Method A, it is surprising that a close comparison exists between Method A and Method B MB values. Apparently the MB activity that is eluted and lost to the BB fraction in Method A is replaced by a nearly equal amount of MM carry-over into the MB fraction.

The reason for isoenzyme carry-over in Method A (but not by following the teachings of the invention—Method B) is believed to be due to the fact that the initial column conditions in Method A are such that the electrical charge characteristics of the serum and ion exchanger are unmatched; whereas they are substantially matched in practicing the invention. This is shown in FIG. 7. Note that the milliequivalents of cations and anions in untreated serum are about 150; while they are substantially the same, or about 130, in the starting buffer of the present invention. In Methd A, however, the milliequivalents are only about 30, which is believed to bring about the undesirable results achieved in following Method A.

Although the invention has been shown in connection with certain specific embodiments, it will be readily apparent to those skilled in the art that various changes in form and arrangement of parts may be made to suit requirements without departing from the spirit and scope of the invention. In this respect, it will be appreciated that while varying concentration of Tris-buffered sodium chloride has been used in the examples given herein, it is possible that other and different buffers may be used with an anion ion exchange agent, just so long as the buffer agent reacts with the ion exchange agent to selectively separate one type of isoenzyme from others. It is also apparent that the separation of other serum isoenzymes such as glutamic oxaloacetate transaminase, acid and alkaline phosphatase and others will be achieved by the ion exchange column chromatographic technique. The following Table V illustrates other systems wherein the invention is applicable.

TABLE V
MINI-COLUMN SEPARATION PROCEDURES FOR SERUM ISOENZYMES AND SPECIFIC PROTEINS

| Enzyme | Ion Exchanger | Serum Volume | Equilibration for Ion Exchanger | No. Isoenzymes Separated |
|---|---|---|---|---|
| Acid Phosphatase | DEAE-Sephadex | 1.0 ml. | 0.05 M Tris-HCl 0.10 M NaCl pH 8.0 | Three |
| Aspartate Transaminase | QAE-Sephadex | 0.5 ml. | 0.05 M Tris-HCl 0.10 M NaCl pH 9.0 | Two |
| Gamma Glutamyl Transpeptitase | DEAE-Sephadex | 0.5 ml. | 0.05 M Tris-HCl 0.10 M NaCl pH 8.0 | Four |
| Amylase | QAE-Sephadex | 0.5 ml. | 0.05 M Tris-HCl 0.10 M NaCl pH 9.0 | Two |
| Aldolase | QAE-Sephadex | 0.5 to 1.0 ml. | 0.05 M Tris-HCl 0.10 M NaCl pH 9.0 | Three |
| Lipoproteins | QAE-Sephadex | 0.2 to 0.5 ml. | 0.07 M Tris-Glycine 0.10 M NaCl pH 9.5 | Four |

I claim as my invention:

1. A method of determining the presence of isoenzymes of different net electrical charges derived from creatine phosphokinase in a sample of blood serum or tissue extracts, comprising the steps of a. equilibrating an ion exchange agent of the amine type based on a polysaccharide matrix with an aqueous buffered alkali metal chloride having about 0.1 molar alkali metal chloride at about pH 8.0 to 9.5 so that the net electrical charge characteristics of the ion exchange agent are similar to those of the blood serum sample in undialyzed, unaltered ionic form or the tissue extract sample in undialyzed, unaltered ionic form;

b. passing said sample of blood serum in undialyzed, unaltered ionic form or tissue extract sample in undialyzed, unaltered ionic form through said equilibrated ion exchange agent and collecting the effluent, then c. passing through said ion exchange agent successive separate volumes of an aqueous buffered alkali metal chloride solution of a first molar ion concentration of about 0.1 and a pH of about 8.0 to 9.5, collecting the effluent separate from the effluent of step (b), then passing through the same column of the ion exchange agent an aqueous buffered alkali metal chloride solution of a second molar ion concentration of about 0.2 and a pH of about 8.0 to 9.5, and collecting the effluent separately from the effluents of step (b) and the first effluent of step (c);

d. assaying each of said separate effluents to determine whether the isoenzymes of creatine phosphokinase are present therein.

2. The method of claim 1 wherein in step (c) an aqueous buffered alkali metal chloride solution of a third molar ion concentration of about 0.3 and a pH of about 7.0 is passed through the same column of ion exchange agent after the said solution containing about 0.2 molar ion concentration is passed through and the effluent therefrom is collected separately from the effluents collected in steps (b) and (c) of claim 1, then assayed for the presence of an isoenzyme of creatine phosphokinase.

3. The method of claim 1 wherein the buffer is a Tris buffer at about 0.05 molar.

4. The method of claim 1 wherein the sample is blood serum in undialyzed, unaltered ionic form.

5. The method of claim 2 wherein the buffer is a Tris buffer at about 0.05 molar.

6. The method of claim 2 wherein the sample is blood serum in undialyzed, unaltered ionic form.

7. The method of claim 1 wherein the ion exchange agent is DEAE-Sephadex.

8. The method of claim 2 wherein the ion exchange agent is DEAE-Sephadex.

9. A method of determining the presence of isoenzymes of different net electrical charges derived from lactate dehydrogenase in a sample of blood serum or tissue extracts, comprising the steps of
   a. equilibrating an ion exchange agent of the amine type based on a polysaccharide matrix with an aqueous buffered alkali metal chloride having about 0.1 molar alkali chloride at about pH 8.0 to 9.5 so that the net electrical charge characteristics of the ion exchange agent are similar to those of the blood serum sample in undialyzed, unaltered ionic form or the tissue extract sample in undialyzed, unaltered ionic form;
   b. passing said sample of blood serum in undialyzed, unaltered ionic form or tissue extract in undialyzed, unaltered form through said equilibrated ion exchange agent and collecting the effluent, then
   c. passing through said ion exchange agent successive separate volumes of an aqueous buffered alkali metal chloride solution of a first molar ion concentration of about 0.1 and a pH of about 8.0 to 9.5, collecting the effluent separate from the effluent of step (b), then passing through the same column of the ion exchange agent an aqueous buffered alkali metal chloride solution of a second molar ion concentration of about 0.2 and a pH of about 8.0 to 9.5 and collecting the effluent separately from the effluents of step (b) and the first effluent of step (c);
   d. assaying each of said separate effluents to determine whether the isoenzymes of lactate dehydrogenase are present therein.

10. The method of claim 9 wherein the buffer is a Tris buffer at about 0.05 M.

11. A method of determining the presence of isoenzymes of different net electrical charges derived from an enzyme selected from the group consisting of acid phosphatase, aspartate transaminase, gamma glutamyl transpeptidase, amylase and aldolase in a sample of blood serum tissue extracts, comprising the steps of
   a. equilibrating an ion exchange agent of the amine type based on a polysaccharide matrix with an aqueous buffered alkali metal chloride having about 0.1 molar alkali metal chloride at about pH 8.0 to 9.5 so that the net electrical charge characteristics of the ion exchange agent are similar to those of the blood serum sample in undialyzed, unaltered ionic form or the tissue extracts sample in undialyzed, unaltered ionic form;
   b. passing said sample of blood serum in undialyzed, unaltered ionic form or tissue extracts in undialyzed, unaltered form through said equilibrated ion exchange agent and collecting the effluent, then
   c. passing through said ion exchange agent successive separate volumes of an aqueous buffered alkali metal chloride solution of a first molar ion concentration of about 0.1 and a pH of about 8.0 to 9.5, collecting the effluent separate from the effluent of step (b), then passing through the same column of the ion exchange agent an aqueous buffered alkali metal chloride solution of a second molar ion concentration of about 0.2 and a pH of about 8.0 to 9.5, and collecting the effluent separately from the effluents of step (b) and the first effluent of step (c);
   d. assaying each of said separate effluents to determine whether the isoenzymes of said enzymes are present therein.

* * * * *